United States Patent
Gers-Barlag et al.

(10) Patent No.: US 6,592,883 B1
(45) Date of Patent: Jul. 15, 2003

(54) EMULSIFIER-FREE FINELY DISPERSE SYSTEMS OF THE WATER-IN-OIL TYPE

(75) Inventors: Heinrich Gers-Barlag, Kummerfeld (DE); Anja Müller, Rümpel (DE); Birgit Groteluschen, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/640,528

(22) Filed: Aug. 17, 2000

(30) Foreign Application Priority Data

Aug. 18, 1999 (DE) .......................................... 199 39 139

(51) Int. Cl.⁷ ................................................ A61K 7/00
(52) U.S. Cl. ...................... 424/401; 424/400; 514/938
(58) Field of Search ................. 424/401, 400; 514/938

(56) References Cited

U.S. PATENT DOCUMENTS 5,314,683 A * 5/1994 Schlossman ................. 424/6.3
5,788,952 A * 8/1998 Gers-Barlag et al. ......... 424/59

FOREIGN PATENT DOCUMENTS

EP 0782846 * 9/1997

* cited by examiner

Primary Examiner—Shelley A. Dodson
(74) Attorney, Agent, or Firm—Norris McLaughlin & Marcus

(57) ABSTRACT

Cosmetic or dermatological preparations which are finely disperse systems of the water-in-oil type, comprising
1. an oil phase,
2. a water phase,
3. a combination of
   a) at least one modified phyllosilicate
   b) and boron nitride, where both the modified phyllosilicate or phyllosilicates and the boron nitride exhibit both hydrophilic and lipophilic properties, i.e. have amphiphilic character and position themselves at the water/oil interface and
4. at most 0.5% by weight of one or more emulsifiers and optionally comprising further cosmetic or pharmaceutical auxiliaries, additives and/or active ingredients.

17 Claims, No Drawings

EMULSIFIER-FREE FINELY DISPERSE SYSTEMS OF THE WATER-IN-OIL TYPE

The present invention relates to emulsifier-free finely disperse systems of the water-in-oil type, preferably as cosmetic or dermatological preparations.

By far the most important type of product in the field of skin care compositions are emulsions. Emulsions are disperse two- or multi-phase systems, cosmetic emulsions consisting of at least one fatty phase (fats and mineral oils, fatty acid esters etc.) and at least one water phase (water, glycerol, glycols etc.), which are finely distributed in one another with the help of emulsifiers. The lipophilic phase of a body care emulsion usually comprises a mixture of oils, fats and waxes, the composition of which is said to significantly influence the product-determining properties such as skin care and feel on the skin.

If the two liquids are water and oil and if oil droplets are finely distributed in water, then this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic character here being determined by the oil.

In order to achieve permanent dispersion of one liquid in another, emulsions in the traditional sense require the addition of a surface-active substance (emulsifier). Emulsifiers have an amphiphilic molecular structure, consisting of a polar (hydrophilic) and a nonpolar (lipophilic) molecular moiety, which are spatially separate from one another. They lower the surface tension between the phases by positioning themselves at the interface between two liquids (they form interfacial films), as a result of which irreversible coalescence of the droplets is prevented. Emulsions are frequently stabilized using emulsifier mixtures.

Traditional emulsifiers can, depending on their hydrophilic molecular moiety, be divided into ionic (anionic, cationic and amphoteric) and nonionic:

The most well-known example of an anionic emulsifier is soap, which is usually the term used for the water-soluble sodium or potassium salts of saturated and unsaturated higher fatty acids.

Important examples of cationic emulsifiers are the quaternary ammonium compounds.

The hydrophilic molecular moiety of nonionic emulsifiers frequently consists of glycerol, polyglycerol, sorbitans, carbohydrates and polyoxyethylene glycols and, in most cases, is linked to the lipophilic molecular moiety via ester and ether bonds. The lipophilic molecular moiety usually consists of fatty alcohols, fatty acids or isofatty acids.

By varying the structure and the size of the polar and nonpolar molecular moiety, the lipophilicity and hydrophilicity of emulsifiers can be varied within wide limits.

A decisive factor for the stability of an emulsion is the correct choice of emulsifiers. In this connection, the characteristics of all the substances present in the system are to be taken into consideration. In the case of, for example, skin care emulsions, polar oil components and, for example, UV filters lead to instability. As well as the emulsifiers, therefore, other stabilizers are also used which, for example, increase the viscosity of the emulsion and/or act as protective colloid.

Cosmetic preparations are essentially used for skin care. The main aim of skin care in the cosmetics sense is to strengthen or rebuild the skin's natural function as the barrier against environmental influences (e.g. dirt, chemicals, microorganisms) and against the loss of endogenous substances (e.g. water, natural fats, electrolytes). If this function becomes impaired, increased resorption of toxic or allergenic substances or attack by microorganisms may result, leading to toxic or allergic skin reactions.

Another aim of skin care is to compensate for the loss by the skin of lipids and water caused by daily washing. This is particularly important where the natural regeneration ability is inadequate. Furthermore, skincare products should protect against environmental influences, in particular against sun and wind, and delay skin ageing.

The harmful effect of the ultraviolet part of solar radiation on the skin is generally known. Depending on their respective wavelength, the rays have different effects on the skin organ: UV-C radiation having a wavelength of less than 290 nm is absorbed by the ozone layer in the earth's atmosphere and is of no physiological importance. By contrast, rays in the range between 290 nm and 320 nm, the UV-B region, cause erythema, simple sunburn or even burns of varying severity. UV-A radiation (320 to 400 nm) is much more harmful than UV-B radiation with regard to the triggering of photodynamic, specifically phototoxic, reactions and chronic changes in the skin. For example, UV-A radiation on its own under very normal everyday conditions is sufficient to damage collagen and elastin fibres within a short period. The harmful effect of UV-B radiation can also be further intensified by UV-A radiation.

In addition, even very low doses of radiation can trigger photochemical reactions. These include, in particular, the formation of free radicals, which in turn can trigger uncontrolled secondary reactions as a result of their high reactivity. In order to prevent such reactions, as well as UV filter substances, it is also possible to additionally add antioxidants and/or free-radical scavengers to cosmetic or dermatological formulations.

Emulsions also play the decisive role in the field of sunscreen formulations. In this connection, preference is given to flowable emulsions, since they can be applied more easily than viscous creams. Most sunscreens are applied in the vicinity of water or during sporting activity (perspiration), for which reason the water resistance of such formulations is to be attributed particular importance. A water-resistant sunscreen protects the user not only after bathing, but also protects him against sunburn during bathing.

In order to achieve high sunscreen factors coupled with very good water resistance, W/O formulations are advantageous. However, W/O emulsions of the prior art frequently have unsatisfactory cosmetic properties. During application, appropriate preparations can leave behind a greasy, shiny and sometimes sticky impression on the skin and—particularly on hairy skin—are difficult to spread. In individual cases, therefore, such preparations may not even be marketable since they are unacceptable to or viewed negatively by the consumer.

An object of the present invention was therefore to remedy the disadvantages of the prior art and to find preparations of the water-in-oil type which, for example, permit the formulation of high sunscreen factors coupled with very good water resistance, but which do not leave behind a greasy or sticky impression on the skin.

In addition, cosmetic preparations are also used as deodorants. Such formulations are used to control body odour which forms when fresh perspiration, which is in itself odourless, is decomposed by microorganisms.

Medicinal topical compositions usually comprise one or more medicaments in an effective concentration. For the sake of simplicity, in order to distinguish clearly between cosmetic and medicinal use and corresponding products, reference is made to the legal provisions of the Federal Republic of Germany (e.g. Cosmetics Directive, Food and Drugs Act).

The use of customary emulsifiers in cosmetic or dermatological preparations is in itself acceptable. Nevertheless, emulsifiers, like ultimately any chemical substance, may in individual instances cause allergic reactions or reactions based on oversensitivity of the user.

For example, it is known that certain light dermatoses are triggered by certain emulsifiers, but also by various fats and simultaneous exposure to sunlight. Such light dermatoses are also called "Mallorca acne". There has thus been no lack of attempts to reduce the amount of customary emulsifiers to a minimum, and in an ideal case even completely.

A reduction in the required amount of emulsifier can, for example, be achieved by taking advantage of the fact that very finely divided solid particles have an additional stabilizing action on an emulsion. This results in an accumulation of the solid substance at the oil/water phase boundary in the form of a layer, as a result of which coalescence of the disperse phases is prevented. Of fundamental importance here are not the chemical properties, but the surface properties of the solid particles.

A relatively new technical development involves stabilizing cosmetic or dermatological preparations only using very finely divided solid particles. Such "emulsifier-free" emulsions are also referred to as Pickering emulsions after their inventor.

Basic experiments have shown that one characteristic of a Pickering emulsion is that the solid particles are arranged at the interface between the two liquid phases, where they form, as it were, a mechanical barrier against the combining of the liquid droplets.

One way of achieving solid stabilization in a cosmetic or dermatological preparation, according to May-Alert (Pharmazie in unserer Zeit [Pharmacy in our Time], Vol. 15. 1986, No. 1, 1–7) for example, is to use emulsifier mixtures which comprise both anionic and cationic surfactants. Since mixing anionic and cationic surfactants always results in the precipitation of insoluble, electroneutral compounds, deliberate precipitation of these neutral surfactants in the oil/water interface makes it possible to achieve additional solids stabilization in the sense of a Pickering emulsion.

In addition, the WO Specification WO-98/42301 describes emulsifier-free finely disperse systems of the water-in-oil type which are stabilized by the addition of micronized inorganic pigments from the group of metal oxides.

However, the prior art was unable to point the way to the present invention.

A further object of the present invention was therefore to develop cosmetic and dermatological bases for cosmetic and dermatological preparations which are characterized by good skin compatibility.

It was also an object of the present invention to provide products with the widest possible variety of applications. For example, the intention was to provide bases for preparation forms such as cleansing emulsions, face care and body care preparations or deodorants and, in particular, light protection agents, and also, for example, preparations against acne and other skin conditions.

A further object of the present invention was to enrich the prior art with cosmetic or dermatological preparations in which any use of emulsifiers of the traditional type can be dispensed with.

Surprisingly, all of these objects are achieved by cosmetic or dermatological preparations which are finely disperse systems of the water-in-oil type, comprising
1. an oil phase,
2. a water phase,
3. a combination of
    a) at least one modified phyllosilicate
    b) and boron nitride, where both the modified phyllosilicate or phyllosilicates and the boron nitride exhibit both hydrophilic and lipophilic properties, i.e. have amphiphilic character and position themselves at the water/oil interface and
4. at most 0.5% by weight of one or more emulsifiers and optionally comprising further cosmetic or pharmaceutical auxiliaries, additives and/or active ingredients.

According to the invention, it is particularly advantageous if the preparations comprise significantly less than 0.5% by weight of one or more emulsifiers. Very particular preference is given to preparations according to the invention which are entirely free from emulsifiers in the traditional sense.

The preparations according to the invention are mixtures of oils or oil-soluble substances and water or water-soluble components, which are stabilized by the addition of the combination according to the invention and do not have to comprise an emulsifier in the traditional sense.

The preparations according to the invention are entirely satisfactory preparations in every respect which, surprisingly, have excellent cosmetic properties, do not leave behind a greasy or sticky impression on the skin, and are characterized by excellent skin compatibility.

Silicates are salts and esters (silicic esters) of orthosilicic acid $[Si(OH)_4]$ and condensation products thereof. Silicates are not only the class of minerals which contain the most types, but are also extremely important from a geological and industrial viewpoint. Over 80% of the earth's crust consists of silicates. Phyllosilicates are (ideally) silicate structures having two-dimensionally infinite layers of $[SiO_4]^{4-}$ tetrahedra, each tetrahedron being bonded to neighbouring tetrahedra by 3 bridging oxygens.

Only approximate chemical formulae can be given for phyllosilicates since they have a large ion-exchange capability, and silicon can be replaced by aluminium, and this in turn can be replaced by magnesium, $Fe^{2+}$, $Fe^{3+}$, Zn and the like. The negative charge of the layers which may result is usually balanced by cations, in particular by $Na^+$ and $Ca^{2+}$ in interlayer positions.

Phyllosilicates can swell by reversible intercalation of water (in a 2- to 7-fold amount) and other substances, such as, for example, alcohols, glycols and the like. Their use as thickeners in cosmetic compositions is, accordingly, known per se. However, the prior art was unable to point the way to the present invention.

Advantageous phyllosilicates which can be used in a combination according to the invention with boron nitride are, for example, those whose greatest expansion direction in the unmodified and unswollen state has, on average, a length of less than 10 μm. For example, the average expansions of the modified phyllosilicate particles used can be 1000 nm×100 nm×1 nm and below. The effective size of the modified phyllosilicate particles in a cosmetic or dermatological formulation naturally depends on the amount of intercalated substances.

Advantageous modified phyllosilicates for the purposes of the present invention are, for example, modified smectites.

Smectites are always very finely particulate (in most cases<2 mm) three-layer clay minerals (2:1 phyllosilicates)

which occur mainly as lamella-shaped, moss-like or spherical aggregates, in which a central layer of octahedrally coordinated cations is sandwiched by two layers of [(Si,Al)O₄] tetrahedra. Smectites are described in an idealized manner by the following structural formula, in which circles filled in white represent silicon and/or aluminium atoms, circles filled in pale grey are oxygen atoms, circles filled in dark grey are hydrogen atoms, and circles filled in black are aluminium, magnesium, iron atoms and/or other exchange cations:

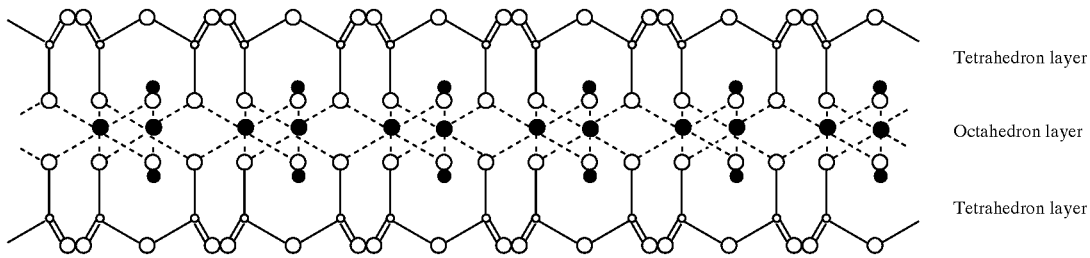

Tetrahedron layer

Octahedron layer

Tetrahedron layer

Advantageous modified smectites are, for example, modified montmorillonites. Montmorillonites are described by the approximated chemical formula $Al_2[(OH)_2/Si_4O_{10}]\cdot n\ H_2O$ or $Al_2O_3\cdot 4SiO_2\cdot H_2O\cdot n\ H_2O$, and are clay minerals belonging to the dioctahedral smectites.

Also particularly advantageous for the purposes of the present invention are, for example, modified hectorites. Hectorites are types of smectites and have the approximate chemical formula $M^+_{0.3}(Mg_{2.7}Li_{0.3})[Si_4O_{10}(OH)_2]$, in which $M^+$ is in most cases $Na^+$.

Also advantageous for the purposes of the present invention are modified bentonites. Bentonites are clays and rocks which contain smectites, especially montmorillonite, as main minerals. The "crude" bentonites are either calcium bentonites (referred to in Great Britain as fuller's earths) or sodium bentonites (also: Wyoming bentonites).

Modified phyllosilicates for the purposes of the present invention are phyllosilicates, in particular the phyllosilicate types already mentioned, whose organophilicity (also: lipophilicity) has been increased, for example by reaction with quaternary ammonium compounds. Such phyllosilicates are also referred to as organophillic phyllosilicates.

Particularly advantageous for the purposes of the present invention are bentones, i.e. organic derivatives of montmorillonites (or bentonites) and/or hectorites, which are prepared by ion-exchange reactions with alkylammonium bases.

Advantageous modified phyllosilicates for the purposes of the present invention are obtainable, for example, by reacting phyllosilicates with quaternium-18. Quaternium-18 is a mixture of quaternary ammonium chloride salts which are described by the following structural formula:

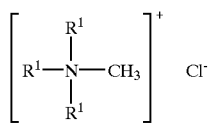

in which
the radicals $R^1$ are independently of one another chosen from the group consisting of methyl and hydrogenated tallow radicals having a chain length of from 12 to 20 carbon atoms.

According to the invention, particular preference is given to stearalkonium hectorite, a reaction product of hectorite and stearalkonium chloride (benzyldimethylstearyl-ammonium chloride), and quaternium-18 hectorite, a reaction product of hectorite and quaternium-18, which are available, for example, under the trade names Bentone 27 and Bentone 38 from Nordmann & Rassmann.

The total amount of one or more modified phyllosilicates in the finished cosmetic or dermatological preparations is advantageously chosen from the range 0.05 to 5.0% by weight, preferably 0.1 to 1.0% by weight, based on the total weight of the preparations.

Advantageous boron nitrides which can be used in a combination according to the invention with one or more modified phyllosilicates are, for example, the boron nitrides listed below:

| Trade name | Obtainable from |
| --- | --- |
| Boron Nitride Powder | Advanced Ceramics |
| Boron Nitride Powder | Sintec Keramik |
| Ceram Blanche | Kawasaki |
| HCST Boron Nitride | Stark |
| Trés BN ® | Carborundum |
| Wacker-Bornitrid BNP | Wacker-Chemie |

It is advantageous to choose the average particle diameter of the boron nitride particles used to be less than 20 μm, particularly advantageously less than 15 μm.

Pickering emulsions for the purposes of the present invention are likewise advantageously stabilized by combinations of one or more modified phyllosilicates with boron nitride particles which have been surface-treated ("coated") to repel water, the intention being for the amphiphilic character to be simultaneously formed or retained.

An advantageous coating of the boron nitride particles consists of dimethylpolysiloxane (also: dimethicone), a mixture of completely methylated, linear siloxane polymers which have been terminally blocked with trimethylsiloxy units. The boron nitride particles treated with dimethicone and obtainable from Carborundum under the trade name Trés BN® UHP 1106, for example, are advantageous.

Also advantageous is a coating of the boron nitride particles with polymethylhydrogen-siloxane, a linear polysiloxane, which is also referred to as methicone. Advantageous boron particles coated with methicone are, for example, those obtainable from Carborundum under the trade name Trés BN® UHP 1107.

The total amount of boron nitride (one or more compounds) in the finished cosmetic or dermatological preparations is advantageously chosen from the range 0.1 to 5.0% by weight, preferably 0.5 to 2.0% by weight, based on the total weight of the preparations.

Although it is particularly preferred to stabilize the preparations according to the invention only by the addition of the combination according to the invention, it may also be advantageous to use further amphiphilic pigments which may also contribute to the stabilization of the Pickering emulsions.

Such pigments are, for example, micronized, inorganic pigments chosen from the group of amphiphilic metal oxides, in particular from the group consisting of titanium dioxide, zinc oxide, silicon dioxide and silicates (e.g. talc), it being possible for the metal oxides to be present individually or as a mixture. In this connection, it is essentially unimportant in which of the potentially naturally occurring modifications the amphiphilic metal oxides used are present.

It is advantageous to choose the average particle diameter of these pigments to be between 1 nm and 200 nm, particularly advantageously between 5 nm and 100 nm.

For the purposes of the present invention, it is advantageous to use, as well as the combination according to the invention, untreated, virtually pure pigment particles, in particular those which can also be used as dye in the foods industry and/or as absorbers of UV radiation in sunscreens. Advantageous examples are the zinc oxide pigments available from Merck, and those available under the trade names Zinkoxid neutral from Haarmann & Reimer or NanoX from Harcros Chemical Group.

According to the invention it is also advantageous to use inorganic pigments which have been surface-treated ("coated") to repel water, the intention being for the amphiphilic character of these pigments to be formed or retained at the same time. This surface treatment may involve providing the pigments with a thin hydrophobic layer by methods known per se.

Such a process, which is described below using titanium dioxide as an example, consists, for example, in producing the hydrophobic surface layer by a reaction in accordance with

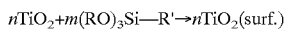

$n\text{TiO}_2 + m(\text{RO})_3\text{Si}—\text{R}' \rightarrow n\text{TiO}_2(\text{surf.})$ n and m are stoichiometric parameters to be used as desired, and R and R' are the desired organic radicals. Particularly advantageous $\text{TiO}_2$ pigments are, for example, those coated with aluminium stearate and obtainable under the trade name MT 100 T from TAYCA.

A further advantageous coating of the additional pigments consists of dimethylpolysiloxane (also: dimethicone), a mixture of completely methylated, linear siloxane polymers which have been terminally blocked with trimethylsiloxy units. Other pigments which are particularly advantageous for the purposes of the present invention are zinc oxide pigments which have been coated in this manner.

It also advantageous if the inorganic pigments used in addition to the combination according to the invention have been coated with a mixture of dimethylpolysiloxane, in particular dimethylpolysiloxane having an average chain length of from 200 to 350 dimethylsiloxane units, and silica gel, which is also referred to as simethicone. It is particularly advantageous if the inorganic pigments have been additionally coated with aluminium hydroxide or hydrated aluminium oxide (also: alumina, CAS No.: 1333-84-2). Particularly advantageous combination partners are titanium dioxides which have been coated with simethicone and alumina, it also be possible for the coating to comprise water. One example thereof is the titanium dioxide available under the trade name Eusolex T2000 from Merck.

It is also advantageous for the purposes of the present invention to use, in addition to the combination according to the invention, a mixture of different inorganic, amphiphilic pigment types, either mixtures within a crystal, for example as iron mixed oxide or talc (magnesium silicate) or else mixtures of two or more types of metal oxide within a preparation. Magnesium silicates are particularly advantageous, for example those available under the trade name Talkum Micron from Grolmann.

The combination according to the invention can also advantageously be combined, for example, with titanium dioxide pigments which have been coated with octylsilanol, and/or with silicon dioxide particles which have been surface-treated to repel water. Suitable silicon dioxide particles are, for example, spherical polyalkylsilsesquioxane particles, as mentioned in European Laid-Open Specification 0 686 391. Such polyalkylsilsesquioxane particles are available, for example, under the trade names Aerosil R972 and Aerosil 200 V from Degussa.

It is further advantageous if, in addition to the combination according to the invention, microfine polymer particles are used which are in the preparation in the form of solids. Favourable examples for the purposes of the present invention are polycarbonates, polyethers, polyethylene, polypropylene, polyvinyl chloride, polystyrene, polyamides, polyacrylates and the like.

According to the invention, microfine polyamide particles, in particular those available under the trade name SP-500 from TORAY, for example, are suitable. Also advantageous are polyamide 6 (also: nylon 6) and polyamide 12- (also: nylon 12) particles. Polyamide 6 is the polyamide [poly($\epsilon$-caprolactam)], built up from $\epsilon$-aminocaproic acid (6-aminohexanoic acid) or $\epsilon$-caprolactam, and polyamide 12 is a poly($\epsilon$-laurolactam) of $\epsilon$-laurolactam. Advantageous examples for the purposes of the present invention are Orgasol® 1002 (polyamide 6) and Orgasole® 2002 (polyamide 12) from ELF ATOCHEM.

Further microfine polymer particles which can be used advantageously in addition to the combination according to the invention are microfine polymethacrylates. Such particles are available, for example, under the trade name POLYTRAP® from DOW CHEMICAL.

It is particularly advantageous, although not obligatory, if the further microfine polymer particles have been surface-coated. This surface treatment can involve providing the polymer particles with a thin hydrophilic layer by processes known per se. Advantageous coatings consist, for example, of titanium dioxide ($\text{TiO}_2$), zirconium dioxide ($\text{ZrO}_2$) or else further polymers, such as, for example, polymethyl methacrylate. Particularly advantageous microfine polymer particles for the purposes of the present invention are, for example, those available by the process described in U.S. Pat. No. 4,898,913 for the hydrophilic coating of hydrophobic polymer particles.

The average particle diameter of the microfine polymer particles used is preferably chosen to be less than 100 $\mu$m, particularly advantageously to be less than 50 $\mu$m. In this connection, it is essentially unimportant in which form (platelets, rods, spherules etc.) the polymer particles used are present.

It is also advantageous if, in addition to the combination according to the invention, amphiphilic modified polysaccharides are used which do not exhibit thickening properties.

Such amphiphilic polysaccharides are obtainable, for example, by reacting starch with mono-, bi- or polyfunctional reagents or oxidizing agents in reactions which proceed in a predominantly polymer-analogous manner.

These reactions are based essentially on modifications of the hydroxyl groups of the polyglucans by etherification, esterification or selective oxidation. This produces, for example, starch ethers and startch esters of general structural formula Structural formula (I)

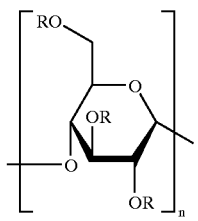

in which R can, for example, be a hydrogen and/or an alkyl and/or aralkyl radical (in the case of starch ethers) or a hydrogen and/or an organic and/or an inorganic acid radical (in the case of starch esters). Starch ethers and starch esters are advantageous modified polysaccharides for the purposes of the present invention.

In addition to the combination according to the invention, it is particularly advantageous to use starch ethers, e.g. those obtainable by etherifying starch with tetramethylol-acetylenediurea and which are referred to as Amylum non mucilaginosum (nonswelling starch).

Also particularly advantageous are starch esters and/or salts thereof, for example sodium and/or aluminium salts of half-esters of starch which have low degrees of substitution, in particular sodium starch n-octenyl succinate of the structural formula (I) in which R is characterized by the following structure

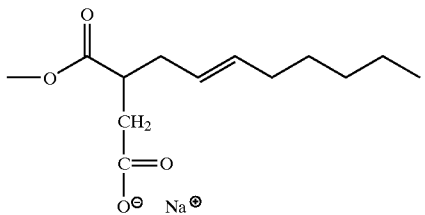

and which is available, for example, under the trade name Amiogume® 23 from CERESTAR, and aluminium starch octenyl succinate, in particular those available under the trade names Dry Flo® Elite LL and Dry Flo® PC from CERESTAR.

It is advantageous to choose the average particle diameter of the modified polysaccharides used together with the combination according to the invention to be less than 20 $\mu$m, particularly advantageously less than 15 $\mu$m.

The list of given modified polysaccharides which can be combined advantageously with the combination according to the invention is not of course intended to be limiting. Modified polysaccharides which are advantageous further pigments for the purposes of the present invention are obtainable in numerous ways, either chemical or physical in nature, which are known per se. For the preparation of such polysaccharides, novel ways are in principle also conceivable. In this connection, it is important that the modified polysaccharides display amphiphilic properties and that they do not have a thickening action.

In all of the abovementioned cases it is advantageous to choose the overall concentration of all further pigments to be greater than 0.05% by weight, particularly advantageously between 0.05% and 30% by weight, based on the total weight of the preparations.

The Pickering emulsions according to the invention can be used as bases for cosmetic or dermatological formulations. The latter can have the customary composition and be used, for example, for the treatment and care of the skin, as lip care product, as deodorant product and as make-up or make-up remover product in decorative cosmetics or as a light protection preparation. For use, the cosmetic and dermatological preparations according to the invention are applied to the skin in a sufficient amount in the manner customary for cosmetics.

Accordingly, for the purposes of the present invention, cosmetics or topical dermatological compositions can, depending on their composition, be used, for example, as skin protection cream, cleansing milk, sunscreen lotion, nourishing cream, day or night cream etc. In some instances, it is possible and advantageous to use the compositions according to the invention as bases for pharmaceutical formulations.

The cosmetic and dermatological preparations according to the invention can comprise cosmetic auxiliaries, as are customarily used in such preparations, e.g. preservatives, bactericides, perfumes, antifoams, dyes, pigments which have a colouring action, thickeners, emollients, moisturizers and/or humectants, fats, oils, waxes or other customary constituents of a cosmetic or dermatological formulation, such as alcohols, polyols, polymers, foam stabilizers, electrolytres, organic solvents or silicone derivatives.

A surprising property of the preparations according to the invention is that they are very good vehicles for cosmetic or dermatological active ingredients into the skin, advantageous active ingredients being antioxidants which are able to protect the skin against oxidative stress.

According to the invention, the preparations advantageously comprise one or more antioxidants. Antioxidants which are favourable, but nevertheless optional, are all antioxidants which are suitable or customary for cosmetic and/or dermatological applications. It is advantageous to use antioxidants as the sole active ingredient class when, for example, any cosmetic or dermatological application is at the fore, such as, for example, the control of oxidative stress of the skin. It is, however, also favourable to provide the stick preparations according to the invention with a content of one or more antioxidants if the intention is for the preparations to have another purpose, e.g. as deodorants or sunscreens.

The antioxidants are particularly advantageously chosen from the group consisting of amino acids (e.g. glycine, histidine, tyrosine, tryptophan) and derivatives thereof, imidazoles, (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximines) in very low tolerated doses (e.g. pmol to $\mu$mol/kg), and also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, glycosylrutin, ferulic acid, furfurylideneglucitol, camosine, butylated hydroxytoluene, butylated hydroxyanisole, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active substances which are suitable according to the invention.

The amount of abovementioned antioxidants (one or more compounds) in the preparations according to the invention is preferably 0.001 to 30% by weight, particularly preferably 0.05 to 20% by weight, in particular 0.1 to 10% by weight, based on the total weight of the preparation.

If vitamin E and/or derivatives thereof are the antioxidant (s), it is advantageous to choose their respective concentrations from the range 0.001 to 10% by weight, based on the total weight of the formulation.

If vitamin A or vitamin A derivatives, or carotenes or derivatives thereof are the antioxidant(s), it is advantageous to choose their respective concentrations from the range 0.001 to 10% by weight, based on the total weight of the formulation.

According to the invention, the active ingredients (one or more compounds) can also very advantageously be chosen from the group of lipophilic active ingredients, in particular from the following group:

Acetylsalicylic acid, atropine, azulene, hydrocortisone and derivatives thereof, e.g. hydrocortisone-17 valerate, vitamins, e.g. ascorbic acid and derivatives thereof, vitamins of the B and D series, very favourably vitamin $B_1$, vitamin $B_{12}$ and vitamin $D_1$, but also bisabolol, unsaturated fatty acids, namely the essential fatty acids (often also called vitamin F), in particular gamma-linolenic acid, oleic acid, eicosapentaenoic acid, docosa-hexaenoic acid and derivatives thereof, chloramphenicol, caffeine, prostaglandins, thymol, camphor, extracts or other products of a vegetable or animal origin, e.g. evening primrose oil, starflower oil or currant seed oil, fish oils, cod-liver oil or also ceramides and ceramide-like compounds and so on.

It is also advantageous to choose the active ingredients from the group of refatting substances, for example purcellin oil, Eucerit® and Neocerit®.

The list of specified active ingredients or active ingredient combinations which can be used in the Pickering emulsions according to the invention should not of course be limiting.

Cosmetic and dermatological preparations which are in the form of a sunscreen are also favourable. In addition to the active ingredient combinations according to the invention, these preferably additionally comprise at least one UV-A filter substance and/or at least one UV-B filter substance. Such formulations can, although it is not necessary, optionally also comprise one or more inorganic pigments as UV filter substances.

Inorganic pigments based on metal oxides and/or other metal compounds which are insoluble or sparingly soluble in water are preferably present, in particular the oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals, and mixtures of such oxides.

An additional content of stabilizing titanium dioxide and/or zinc oxide particles can of course also be advantageous, but is not necessary for the purposes of the present invention.

For the purposes of the present invention, it is also advantageous to prepare cosmetic and dermatological preparations whose main purpose is not protection against sunlight, but which nevertheless contain UV protection substances. Thus, for example, UV-A and UV-B filter substances are usually incorporated into day creams.

Also, UV protectants, like antioxidants, and if desired, preservatives, provide effective protection of the preparations themselves against spoilage.

Preparations according to the invention advantageously comprise substances which absorb UV radiation in the UV-A and UV-B region, the total amount of filter substances being, for example, from 0.1% by weight to 30% by weight, preferably from 0.5 to 20% by weight, in particular from 1.0 to 15% by weight, based on the total weight of the preparations, in order to provide cosmetic preparations which protect the hair and the skin from the entire range of ultraviolet radiation. They can also be used as sunscreens for the hair or the skin.

Advantageous UV-A filter substances for the purposes of the present invention are dibenzoyl methane derivatives, in particular 4-(tert-butyl)-4'-methoxydibenzoylmethane (CAS No. 70356-09-1), which is sold by Givaudan under the name Parsole® 1789 and by Merck under the trade name Eusolex® 9020.

Further advantageous UV-A filter substances are phenylene-1,4-bis-(2-benzimidazyl)-3,3'-5,5'-tetrasulphonic acid:

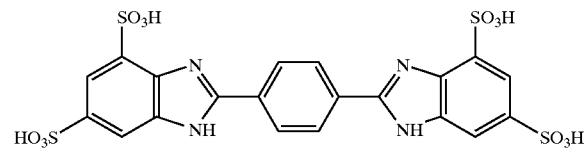

and its salts, particularly the corresponding sodium, potassium or triethanolammonium salts, in particular phenylene-1,4-bis-(2-benzimidazyl)-3,3'-5,5'-tetrasulphonic bis-sodium salt:

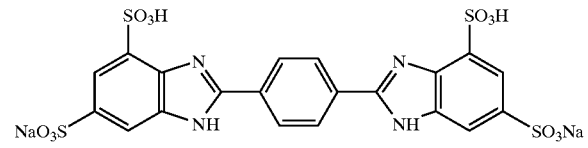

and 1,4-di(2-oxo-10-sulpho-3-bornylidenemethyl)benzene and salts thereof (in particular the corresponding 10-sulphato compounds, in particular the corresponding sodium, potassium or triethanolammonium salt), which is also referred to as benzene-1,4-di(2-oxo-3-bornylidenemethyl-10-sulphonic acid) and is characterized by the following structure:

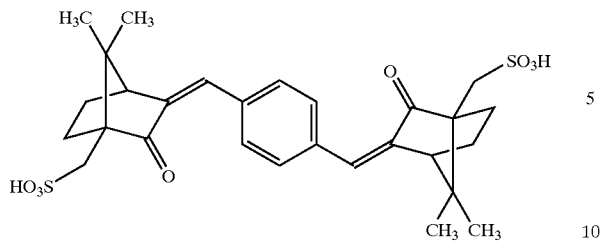

Advantageous UV filter substances for the purposes of the present invention are also broad-band filters, i.e. filter substances which absorb both UV-A and also UV-B radiation.

Advantageous broad-band filters and/or UV-B filter substances are, for example, bisresorcinyltriazine derivates having the following structure:

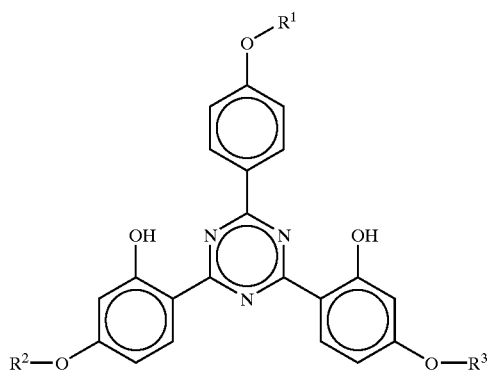

where $R^1$, $R^2$ and $R^3$ independently of one another are chosen from the group of branched and unbranched alkyl groups having 1 to 10 carbon atoms, or are a single hydrogen atom. Particular preference is given to 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH and to tris(2-ethylhexyl) 4,4',4"-(1,3,5-triazine-2,4,6-triyltriimino)trisbenzoate, synonym: 2,4,6-tris[anilino-(p-carbo-2'-ethyl-1'-hexyloxy)]-1,3,5-triazine (INCI: Octyl Triazone), which is marketed by BASF Aktiengesellschaft under the trade name UVINUL® T 150.

Other UV filter substances, which have the structural formula

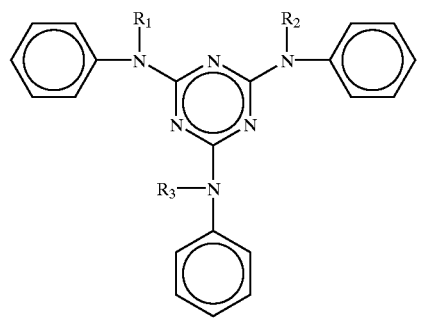

are also advantageous UV filter substances for the purposes of the present invention, for example the s-triazine derivatives described in European Laid-Open Specification EP 570 838 A1, whose chemical structure is expressed by the generic formula

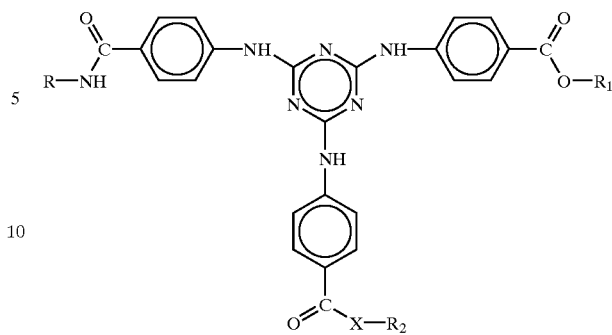

where

R is a branched or unbranched $C_1$–$C_{16}$-alkyl radical, a $C_5$–$C_{12}$-cycloalkyl radical, optionally substituted with one or more $C_1$–$C_4$-alkyl groups, X is an oxygen atom or an NH group, $R_1$ is a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

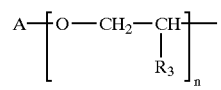

in which

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, $R_2$ is a branched or unbranched $C_1$–$C_{18}$-alkyl radical, a $C_5$–$C_{12}$-cycloalkyl radical, optionally substituted by one or more $C_1$–$C_4$-alkyl groups, when X is the NH group, and a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

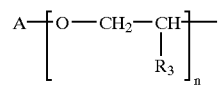

in which

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, when X is an oxygen atom.

A particularly preferred UV filter substance for the purposes of the present invention is also an unsymmetrically substituted s-triazine, the chemical structure of which is expressed by the formula

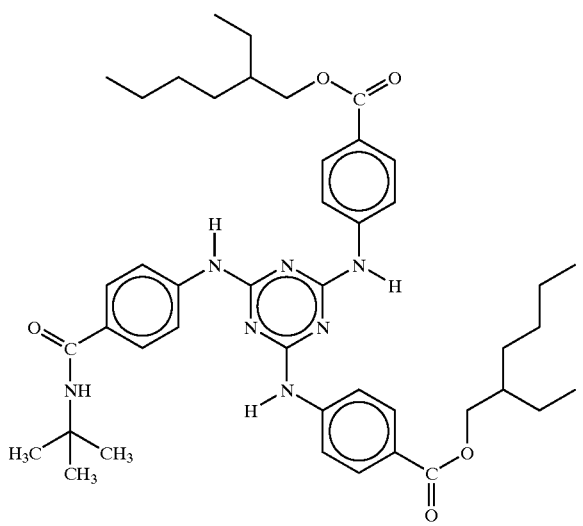

and which is also referred to below as dioctylbutylamidotriazone (INCI: dioctylbutamidotriazone) and is available under the trade name UVASORB HEB from Sigma 3V.

European Laid-Open Specification 775 698 also describes preferred bisresorcinyltriazine derivatives, the chemical structure of which is expressed by the generic formula

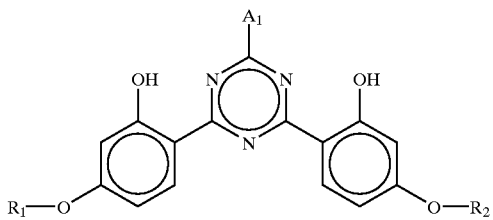

where $R_1$, $R_2$ and $A_1$ represent very different organic radicals.

Also advantageous for the purposes of the present invention are 2,4-bis{[4-(3-sulphonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis-{[4-(2-ethylhexyloxy)-2-hydroxy]phenyl}-6-(1-methylpyrrol-2-yl)-1,3,5-triazine, 2,4-bis{[4-tris(trimethylsiloxysilylpropyloxy)-2-hydroxy]phenyl}-6-(4-methoxyphenyl)-1,3,5-triazine, 2,4-bis{[4-(2"-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2"-methylpropyloxy)-2-hydroxy]phenyl}-6-(4-methoxyphenyl)-1,3,5-triazine.

An advantageous broad-band filter for the purposes of the present invention is 2,2'-methylenebis(6-(2H-benzotriazol-2-yl)-4-(1,1,3,3-tetramethylbutyl)phenol), which is characerized by the chemical structural formula

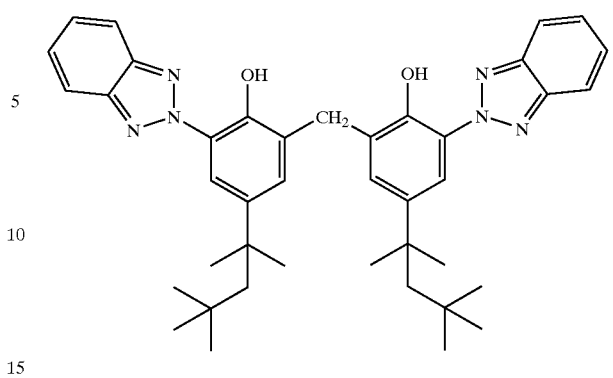

and is available under the trade name Tinosorb® M from CIBA-Chemikalien GmbH.

Another advantageous broad-band filter for the purposes of the present invention is 2-(2H-benzotriazol-2-yl)-4-methyl-6-[2-methyl-3-[1,3,3,3-tetramethyl-1-[(trimethylsilyl)-oxy]disiloxanyl]propyl]phenol (CAS No.: 155633-54-8) having the INCI name Drometrizole Trisiloxane, which is characterized by the chemical structural formula

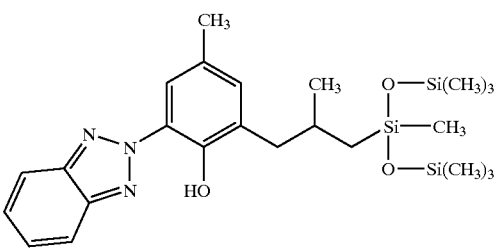

The UV-B filters can be oil-soluble or water-soluble. Examples of advantageous oil-soluble UV-B filter substances are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

2,4,6-trianilino(p-carbo-2'-ethyl-1'-hexyloxy)-1,3,5-triazine;

esters of benzalmalonic acid, preferably di(2-ethylhexyl) 4-methoxybenzalmalonate, esters of cinnamic acid, preferably 2-ethylhexyl 4-methoxycinnamate, isopentyl 4-methoxycinnamate;

derivates of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Examples of advantageous water-soluble UV-B filter substances are:

salts of 2-phenylbenzimidazole-5-sulphonic acid, such as its sodium, potassium or its triethanolammonium salt, and also the sulphonic acid itself;

sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)-sulphonic acid and salts thereof.

A further light protection filter substance which can be used advantageously according to the invention is ethylhexyl 2-cyano-3,3-diphenylacrylate (octocrylene), which is available from BASF under the name Uvinul® N 539 and is characterized by the following structure:

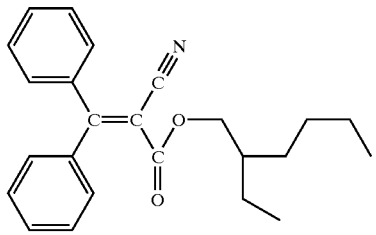

It can also be of considerable advantage to use polymer-bonded or polymeric UV filter substances in the preparations according to the present invention, in particular those described in WO-A-92/20690.

In some instances, it can also be advantageous to incorporate further UV-A and/or UV-B filters in accordance with the invention into cosmetic or dermatological preparations, for example certain salicylic acid derivatives, such as 4-isopropylbenzyl salicylate, 2-ethylhexyl salicylate (=octyl salicylate), homomenthyl salicylate.

The list of given UV filters which can be used for the purposes of the present invention is not of course intended to be limiting.

Preparations according to the invention can also advantageously be used as bases for cosmetic deodorants and antiperspirants, so that a particular embodiment of the present invention relates to Pickering emulsions as bases for cosmetic deodorants.

Cosmetic deodorants are used to control body odour which forms when fresh sweat, which is in itself odourless, is decomposed by microorganisms. Customary cosmetic deodorants are based on various modes of action.

In antiperspirants, astringents, mainly aluminium salts, such as aluminium hydroxychloride (aluminium chlorohydrate), can reduce sweat formation.

The use of antimicrobial substances in cosmetic deodorants can reduce the bacterial flora of the skin. In an ideal situation, only the microorganisms which cause the odour would be effectively reduced. The flow of sweat itself is not influenced as a result, and in ideal circumstances, only microbial decomposition of sweat is stopped temporarily.

The combination of astringents and antimicrobial active substances in one and the same composition is also common.

All active ingredients common for deodorants or antiperspirants can advantageously be used, for example odour concealers, such as customary perfume constituents, odour-absorbers, for example the phyllosilicates described in DE 40 09 347, of these in particular montmorillonite, kaolinite, illite, beidellite, nontronite, saponite, hectorite, bentonite, smectite, and also, for example, zinc salts of ricinoleic acid. Antibacterial agents are also suitable to be incorporated into the W/O emulsion sticks according to the invention. Advantageous substances are, for example, 2,4,4'-trichloro-2'-hydroxy diphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol) and also the active ingredients or active ingredient combinations described in Patent Laid-Open Specifications DE 37 40 186, DE 39 38 140, DE 42 04 321, DE 42 29 707, DE 43 09 372, DE 44 11 664, DE 195 41 967, DE 195 43 695, DE 195 43 696, DE 195 47 160, DE 196 02 108, DE 196 02 110, DE 196 02 111, DE 196 31 003, DE 196 31 004 and DE 196 34 019, and the patent specifications DE-42 29 737, DE-42 37 081, DE-43 24 219, DE-44 29 467, DE-44 23 410 and DE-195 16 705. Sodium hydrogencarbonate can also be used advantageously.

The list of specified active ingredients and active ingredient combinations which can be used the novel Pickering emulsions is of course not intended to be limiting.

The cosmetic deodorants according to the invention can be in the form of aqueous, cosmetic preparations which can be applied from standard containers.

The amount of antiperspirant active ingredients or deodorants (one or more compounds) in the preparations is preferably from 0.01 to 30% by weight, particularly preferably from 0.1 to 20% by weight, in particular 1 to 10% by weight, based on the total weight of the preparation.

The sticks according to the invention are additionally excellent vehicles for dermatological active ingredients. In particular, they are suitable as carriers for substances effective against acne. Acne is a skin disorder with many forms and causes, characterized by noninflamed and inflamed bumps, originating from blocked hair follicles (comedones) which can lead to the formation of pustules, abscesses and scars. The most frequent is Acne vulgaris, which occurs predominantly in puberty. Causative conditions for Acne vulgaris are the keratinization and blocking of the hair follicle opening, the production of sebum, which is dependent on the level of male sex hormones in the blood, and the production of free fatty acids and tissue-damaging enzymes by bacteria (*Propionibacterium acnes*).

It is therefore advantageous to add to the preparations according to the invention, substances which are effective against acne, which are, for example effective against *Propionibacterium acnes* (for example those described in DE-A 42 29 707, DE-A 43 05 069, D-A 43 07 976, DE-A 43 37 711, DE-A 43 29 379) but also other substances which are effective against acne, for example all-trans-retinoic acid, 13-cis-retinoic acid and related substances) or antiinflammatory active ingredients, for example batyl alcohol (α-octadecyl glyceryl ether), selachyl alcohol (α-9-octadecenyl glyceryl ether), chimyl alcohol (α-hexadecyl glyceryl ether) and/or bisabolol and antibiotics and/or keratolytics.

Keratolytics are substances which soften keratinized skin (such as, for example, warts, corns, calluses and the like) so that it can be removed more easily or so that it falls off or peels off.

All of the common substances effective against acne can be used advantageously, in particular benzoyl peroxide, bituminosulphonates (ammonium, sodium and calcium salts of shale oil sulphonic acids), salicylic acid (2-hydroxybenzoic acid), miconazole (1-[2-(2,4-dichlorobenzyloxy)-2-(2,4-dichlorophenyl)ethyl]imidazole) and derivatives, adapalene (6-[3-(1-adamantyl)-4-methoxyphenyl]-2-naphthoic acid), azelaic acid (nonanedioic acid), mesulfene (2,7-dimethylthianthrene, $C_{14}H_{12}S_2$) and aluminium oxide, zinc oxide and/or finely dispersed sulphur.

The amount of antiacne agents (one or more compounds) in the preparations is preferably from 0.01 to 30% by weight, particularly preferably 0.1–20% by weight, in particular 1–10% by weight, based on the total weight of the preparation.

The examples below serve to illustrate the present invention without limiting it. The numerical values in the examples are percentages by weight, based on the total weight of the respective preparations.

EXAMPLES

|  | 1 | 2 | 3 | 4 | 5 | 6 | 7 |
|---|---|---|---|---|---|---|---|
| Bentone 38 ® | 0.5 | 1 | 0.2 |  | 0.2 |  | 0.5 |
| Bentone 27 ® |  |  | 0.3 | 0.7 |  | 0.3 |  |
| Boron nitride | 0.5 | 2 | 1 | 3 | 5 | 1 | 1 |
| Polyglyceryl-2 dipoly-hydroxystearate |  |  |  |  | 0.2 |  |  |
| Cetyldimethicone copolyol |  |  |  |  |  | 0.3 |  |
| PEG-30 dipolyhydroxy-stearate |  |  |  |  |  |  | 0.2 |
| Caprylic/capric triglyceride | 10 | 5 |  |  |  | 7 |  |
| Octyldodecanol |  |  | 10 | 10 |  | 5 |  |
| Dicaprylyl ether | 5 | 5 | 5 |  |  | 5 |  |
| Cetearyl isononanoate |  |  | 2 |  |  |  |  |
| Dimethicone | 2 | 2 | 5 | 2 | 5 |  | 5 |
| Mineral oil | 5 | 5 |  | 10 | 5 | 5 | 2 |
| Isohexadecane |  | 2 | 3 |  | 5 |  |  |
| Hydrogenated polyisobutene | 2 |  | 3 | 5 |  | 5 |  |
| Butylene glycol dicaprylate/caprate |  | 2 | 5 | 5 | 5 |  | 8 |
| C$_{12-15}$ Alkylbenzoate | 7 | 3 |  | 3 | 5 |  | 10 |
| Vitamin E acetate | 0.5 | 0.5 | 0.5 | 0.5 |  | 0.5 |  |
| Dioctylbutamidotriazone |  |  |  |  | 3 | 1 |  |
| Octocrylene |  | 5 |  |  |  | 6 | 5 |
| Octyltriazone | 1 |  |  |  |  |  |  |
| Methylbenzylidenecamphor | 2 | 4 |  |  | 2 |  | 4 |
| Butylmethoxydibenzoyl-methane | 2 |  |  |  | 2 |  | 2 |
| Titanium dioxide | 1 |  |  | 5 | 4 |  | 2 |
| Zinc oxide |  |  |  | 5 |  |  |  |
| Aerosil R972 ® |  | 0.5 |  |  |  | 0.5 |  |
| Preservative | 0.5 | 0.5 | 0.5 | 0.5 | 0.5 | 0.5 | 0.5 |
| Glycerol | 3 | 5 | 10 | 10 | 5 | 10 | 5 |
| MgSO$_4$ |  |  |  |  | 1 | 1 |  |
| NaCl | 0.5 | 1 | 0.2 |  |  |  | 1 |
| Phenylbenzimidazole-sulphonic acid |  |  |  | 2 |  |  | 4 |
| Sodium hydroxide solution, 45% |  |  |  | 0.8 |  |  | 1.3 |
| Water | ad 100 | ad 100 | ad 100 | ad 100 | ad 100 | ad 100 | ad 100 |

What is claimed is:

1. A cosmetic or dermatological preparation, which preparation is a finely dispersed water-in-oil system, said preparation comprising:
   a) an oil phase;
   b) a water phase;
   c) a combination of:
      i) at least one modified phyllosilicate; and
      ii) boron nitride; where both said phyllosilicate and said boron nitride have both hydrophilic and lipophilic properties resulting in an amphiphilic character, and both said modified phyllosilicate and said boron nitride position themselves at an interface of said water phase and said oil phase;
   d) at most 0.5% by weight of one or more emulsifiers; and
   e) optionally one or more cosmetic or pharmaceutical auxiliaries, additives and/or active substances.

2. The cosmetic or dermatological preparation according to claim 1, which is emulsifier-free.

3. The cosmetic or dermatological preparation according to claim 1, which further comprises a content of one or more cosmetic or pharmaceutical auxiliaries, additives and/or active substances.

4. The cosmetic or dermatological preparation according to claim 1, which comprises one or more phyllosilicates in an amount between 0.05 and 5.0% by weight based on the total weight of the preparation.

5. The cosmetic or dermatological preparation according to claim 4, which comprises one or more phyllosilicates in an amount between 0.1 and 1.0% by weight based on the total weight of the preparation.

6. The cosmetic or dermatological preparation according to claim 1, which comprises one or more boron nitrides in an amount between 0.1 and 5.0% by weight based on the total weight of the preparation.

7. The cosmetic or dermatological preparation according to claim 6, which comprises one or more boron nitrides in an amount between 0.5 and 2.0% by weight based on the total weight of the preparation.

8. The cosmetic or dermatological preparation according to claim 1, which, in addition to the combination of one or more modified phyllosilicates and boron nitride, comprises one or more further pigments.

9. The cosmetic or dermatological preparation according to claim 8, wherein the one or more further pigments are one or more pigments selected from the group consisting of modified polysaccharides, microfine polymer particles and micronized, inorganic pigments.

10. The cosmetic or dermatological preparation according to claim 9, wherein the micronized, inorganic pigments are selected from the group consisting of amphiphilic metal oxides.

11. The cosmetic or dermatological preparation according to claim 10, wherein the amphiphilic metal oxides are selected from the group consisting of titanium dioxide, zinc oxide, iron oxides, iron mixed oxides, silicon dioxide, and silicates.

12. The cosmetic or dermatological preparation according to claim 1, which further comprises one or more unsymmetrically substituted s-triazine derivatives.

13. The cosmetic or dermatological preparation according to claim 12, which comprises at least one unsymmetrically substituted s-triazine derivative selected from the group consisting of 2,4-bis-{[4-2-ethylhexyloxy)-2-hydroxy]phenyl}-6-(4-methoxyphenyl)-1,3,5-triazine and dioctylbutylamidotriazone.

14. The cosmetic or dermatological preparation according to claim 1, which further comprises one or more sulfonated UV filter substances.

15. The cosmetic or dermatological preparation according to claim 14, wherein the one or more sulfonated UV filter substances are selected from the group consisting of phenylene-1,4-bis(2-benzimidazyl)-3,3'-5,5'-tetrasulfonic acid and salts thereof, benzene-1,4-di(2-oxo-3-bornylidenemethyl-10-sulfonic acid) and salts thereof, 2-phenylbenzimidazole-5-sulfonic acid and salts thereof, and sulfonic acid derivatives of 3-benzylidenecanphor and salts thereof.

16. The cosmetic or dermatological preparation according to claim 1, which further comprises one or more additives or active substances selected from the group consisting of antioxidants, astringents, antimicrobially active substances, and substances active against acne.

17. A method of caring for skin comprising applying thereto an effective amount therefor of a cosmetic or dermatological preparation according to claim 1.

* * * * *